US006503913B1

(12) United States Patent
Goldmann et al.

(10) Patent No.: US 6,503,913 B1
(45) Date of Patent: Jan. 7, 2003

(54) 2-HETEROCYCLICALLY SUBSTITUTED DIHYDROPYRIMIDINES

(75) Inventors: Siegfried Goldmann, Wuppertal (DE); Jürgen Stoltefuss, Haan (DE); Arnold Paessens, Haan (DE); Erwin Graef, Velbert (DE); Stefan Lottmann, Wuppertal (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/673,597

(22) PCT Filed: Apr. 7, 1999

(86) PCT No.: PCT/EP99/02345

§ 371 (c)(1),
(2), (4) Date: Oct. 18, 2000

(87) PCT Pub. No.: WO99/54329

PCT Pub. Date: Oct. 28, 1999

(30) Foreign Application Priority Data

Apr. 18, 1998 (DE) .......................................... 198 17 262

(51) Int. Cl.⁷ .................... C07D 417/04; C07D 417/14; A61K 31/506
(52) U.S. Cl. ....................... 514/256; 544/333; 544/327; 544/328
(58) Field of Search .......................... 514/256; 544/333, 544/327, 328

(56) References Cited

U.S. PATENT DOCUMENTS

| 3,787,444 A | 1/1974 | Gosteli ........................ 260/327 |
| 3,956,395 A | 5/1976 | Meyer ......................... 260/607 |
| 4,822,798 A | 4/1989 | Stoltefuss et al. .......... 514/255 |

FOREIGN PATENT DOCUMENTS

EP 0103796 3/1984

OTHER PUBLICATIONS

Adler, R., and Becker, H.–D., "Zur Slektiven Oxydation von Benzylalkoholen", Acta Chem. Scand., 15(4):849–852 (1961).
Borrmann, D., "Umsetzungen von Diketen mit Alkoholen, Phenolen and Mercaptanen", in Houben–Weyl, Methoden der Organischen Chemie, vol. 7(4), pp. 230–232 (1968).
Glickman, S.A., and Cope, A. C., "Structure of β–Amino Derivatives of α,β–Unsaturated Lactones and Esters", J. Am. Chem. Soc., 67: 1017–1020 (Jun. 1945).
Harris, T. D., and Roth, G. P., "Ortho Lithiation via a Cabonyl Synthon", J. Org. Chem., 44(12): 2004–2007 (1979).
Jones, G., "The Knoevenagel Condensation" in Organic Reactions, vol. 15, Chapter 2, John Wiley & Sons, Inc. eds., New York, London, Sydney (1967).
Jones, G., and Jones, D. G., "Thiazolopyridinium Salts. Part I. Synthesis of Some Thiazolo[3,2–a]–pyridinium Salts", J. Chem. Soc., (C): 515–518 (1967).
Korba, B. E., and Gerin, J.L., "Use of a standardized cell culture assay to assess activities of nucleoside analogs against hepatitis B virus replication", Antiviral Res., 19: 55–70 (1992).
Miyano, M. Muraki, S., Kusunoki, T., Morita, T., and Matsui, M., "Syntheses of several new compounds related to rotenoids (benzalacetones, o–benzyloxypehylacetonitrile, and chromans)", Heterocycles Compounds, 37: 13929c (1963).
Oikawa, Y., Sugano, K., and Yonemitsu, O., "Meldrum's Acid Organic Synthesis. 2. A General and Versatile Synthesis of β–Keto Esters", J. Org. Chem.,43(10): 2087–2090 (1978).
Papadopoulos, E. P., Jarrar, A., and Issiorides, C. H., "Oxidations with Manganese Dioxide",J. Org. Chem., 31: 615–616 (Feb. 1966).
Sells, M. A., Chen, M.–L., and Acs, G., "Production of Hepatitis B Virus Particles in Hep G2 Cells Transfected with Cloned Hepatitis B Virus DNA", Proc. Natl. Acad. Sci., USA, 84: 1005–1009 (Feb. 1987).
Shriner, R. L., and Neumann, F. W., "The Chemistry of Amidines" in Chemical Reviews, vol. 35, published by the American Chemical Society, The Williams & Wilkins Co. eds., Baltimore, U.S.A. (1944).
Söll H., "Umwandlung von primären and sekundären Aminen", in Houben–Weyl, Methoden der Organischen Chemie, vol. 11(2), pp. 38–39 (1958).

*Primary Examiner*—John M. Ford
(74) *Attorney, Agent, or Firm*—Jerrie L. Chiu

(57) ABSTRACT

The invention relates to new 2-heterocyclically substituted dihydropyrimidines, medicaments which contain these 2-heterocyclically substituted dihydropyrimidines, and a process for preparation of medicaments. The invention furthermore relates to the use of the 2-heterocyclically substituted dihydropyrimidines for the production of a medicament, in particular for the treatment of acute or chronic viral diseases, in particular for the production of a medicament for the treatment of acute or chronic hepatitis B infections.

5 Claims, No Drawings

2-HETEROCYCLICALLY SUBSTITUTED DIHYDROPYRIMIDINES

The present invention relates to new 2-heterocyclically substituted dihydropyrimidines, processes for their preparation and their use as medicaments, in particular as medicaments for the treatment and prophylaxis of hepatitis B.

The publication EP 103 796 A2 has already disclosed dihydropyrimidines having an action affecting the circulation.

The present invention relates to new 2-heterocyclically substituted dihydropyrimidines of the general formula (I)

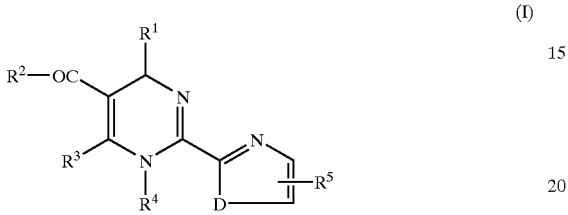

or its isomeric form (Ia)

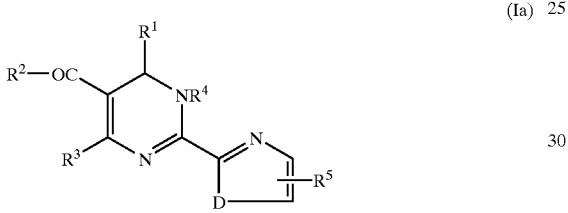

in which
$R^1$ represents phenyl, furyl, thienyl, pyridyl, cycloalkyl having 3 to 6 carbon atoms or a radical of the formula

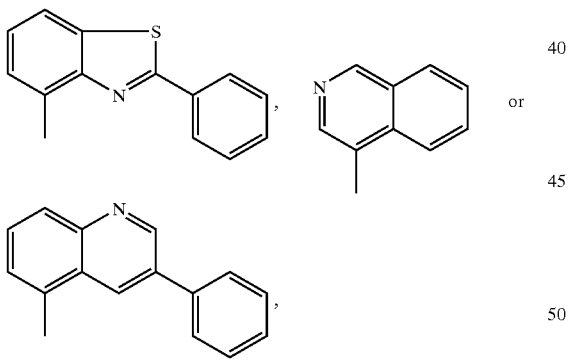

where the abovementioned ring systems are optionally monosubstituted or polysubstituted in an identical or different manner by substituents selected from the group consisting of halogen, trifluoromethyl, nitro, cyano, trifluoromethoxy, carboxyl, hydroxyl, ($C_1$–$C_6$)-alkoxy, ($C_1$–$C_6$)-alkoxycarbonyl and ($C_1$–$C_6$)-alkyl, which for its part can be substituted by aryl having 6 to 10 carbon atoms or halogen,
and/or the ring systems mentioned are optionally substituted by groups of the formula —S—$R^6$, $NR^7R$, CO—$NR^9R^{10}$, $SO_2$—$CF_3$ and —A—$CH_2$—$R^{11}$,
in which
$R^6$ denotes phenyl which is optionally substituted by halogen, $R^7$, $R^8$, $R^9$ and $R^{10}$ are identical or different and denote hydrogen, phenyl, hydroxy-substituted phenyl, hydroxyl, ($C_1$–$C_6$)-acyl or ($C_1$–$C_6$)-alkyl, which for its part can be substituted by hydroxyl, ($C_1$–$C_6$)-alkoxycarbonyl, phenyl or hydroxy-substituted phenyl,
A denotes a radical O, S, SO or $SO_2$,
$R^{11}$ denotes phenyl which is optionally mono- to polysubstituted, in an identical or different manner, by substituents selected from the group consisting of halogen, nitro, trifluoromethyl, ($C_1$–$C_6$)-alkyl and ($C_1$–$C_6$)-alkoxy,
$R^2$ represents a radical of the formula —$OR^{12}$ or —$NR^{13}R^{14}$,
in which
$R^{12}$ denotes hydrogen, ($C_1$–$C_6$)-alkoxycarbonyl or a straight-chain, branched or cyclic, saturated or unsaturated ($C_1$–$C_8$)-hydrocarbon radical which optionally contains one or two identical or different hetero chain members from the group consisting of O, CO, NH, —N—($C_1$–$C_4$)-alkyl, —N—(($C_1$–$C_4$)-alkyl)$_2$, S and $SO_2$ and which is optionally substituted by halogen, nitro, cyano, hydroxyl, aryl having 6 to 10 carbon atoms or aralkyl having 6 to 10 carbon atoms, heteroaryl or a group of the formula —$NR^{15}R^{16}$,
in which
$R^{15}$ and $R^{16}$ are identical or different and denote hydrogen, benzyl or ($C_1$–$C_6$)-alkyl,
$R^{13}$ and $R^{14}$ are identical or different and denote hydrogen, ($C_1$–$C_6$)-alkyl or cycloalkyl having 3 to 6 carbon atoms,
$R^3$ represents hydrogen, amino or
a radical of the formula

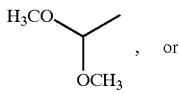

formyl, cyano or trifluoromethyl, or
a straight-chain, branched or cyclic, saturated or unsaturated hydrocarbon radical having up to 8 carbon atoms, which is optionally mono- or polysubstituted, in an identical or different manner, by aryloxy having 6 to 10 carbon atoms, azido, cyano, hydroxyl, carboxyl, ($C_1$–$C_6$)-alkoxycarbonyl, a 5- to 7-membered heterocyclic ring, ($C_1$–$C_6$)-alkylthio, ($C_1$–$C_6$)-alkoxy, which for its part can be substituted by azido or amino, and/or is substituted by triazolyl which for its part can be substituted up to 3 times by ($C_1$–$C_6$)-alkoxycarbonyl,
and/or can be substituted by groups of the formula —$OSO_2$—$CH_3$ or $(CO)_a$—$NR^{17}R^{18}$,
in which
a denotes a number 0 or 1,
$R^{17}$ and $R^{18}$ are identical or different and denote hydrogen or aryl, aralkyl having 6 to 10 carbon atoms,
or denote ($C_1$–$C_6$)-alkyl which is optionally substituted by ($C_1$–$C_6$)-alkoxycarbonyl, hydroxyl, phenyl or benzyl, where phenyl or benzyl are optionally mono- or polysubstituted, in an identical or different manner, by hydroxyl, carboxyl ($C_1$–$C_6$)-alkyl or ($C_1$–$C_6$)-alkoxy, or ($C_1$–$C_6$)-alkyl is optionally substituted by groups of the formula NH—CO—$CH_3$ or NH—CO—$CF_3$, $R^4$ represents hydrogen, $(C_1-C_4)$-alkyl, acetyl or benzoyl, D represents an oxygen or sulphur atom, $R^5$ represents hydrogen, halogen or straight-chain or branched alkyl having up to 6 carbon atoms, and their salts.

Compounds of the general formulae (I) and (Ia) according to the invention are preferred in which $R^1$ represents phenyl, furyl, thienyl, pyridyl, cyclopentyl or cyclohexyl, where the abovementioned ring systems are optionally substituted one or 2 times, in an identical or different manner, by substituents selected from the group consisting of halogen, trifluoromethyl, nitro, $SO_2-CF_3$, methyl, cyano, trifluoromethoxy, carboxyl, methoxycarbonyl or radicals of the formulae $-CO-NH-CH_2-C(CH_3)_3$, $-CO-NH(CH_2)_2OH$, $-CO-NH-CH_2-C_6H_5$, $-CO-NH-C_6H_5$, $-CO-NH-(pOH)-C_6H_4$, $-O-CH_2-C_6H_5$ or $-S-pCl-C_6H_4$, $R^2$ represents a radical of the formula $-OR^2$ or $-NR^{13}R^{14}$, in which $R^{12}$ denotes hydrogen, $(C_1-C_4)$-alkenyl or $(C_1-C_4)$-alkyl, which is optionally substituted by pyridyl, cyano, phenoxy, benzyl or by a radical of the formula $-NR^{15}R^{16}$, in which $R^{15}$ and $R^{16}$ are identical or different and denote hydrogen, methyl or ethyl, $R^{13}$ and $R^{14}$ are identical or different and denote hydrogen, methyl, ethyl or cyclopropyl, $R^3$ represents hydrogen or a radical of the formula

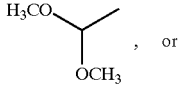, or represents formyl, cyano, trifluoromethyl or cyclopropyl, or represents $(C_1-C_4)$-alkyl which is optionally substituted by radicals of the formula $-SO_2CH_3$, $-NH-CO-CH_3$, $-NH-CO-CF_3$, fluorine, chlorine, $(C_1-C_3)$-alkoxycarbonyl or hydroxyl, O and/or alkyl is optionally substituted by groups of the formula $-OSO_2-CH_3$ or $(CO)_a-NR^{17}R^{18}$, in which a denotes a number 0 or 1, $R^{17}$ and $R^{18}$ are identical or different and denote hydrogen, phenyl or benzyl, or denote $C_1-C_4$-alkyl which is optionally substituted by $(C_1-C_4)$-alkoxycarbonyl, hydroxyl, phenyl or benzyl, where phenyl or benzyl are optionally mono- or polysubstituted, in an identical or different manner, by hydroxyl, carboxyl, $(C_1-C_4)$-alkyl or $(C_1-C_4)$-alkoxy, and/or $(C_1-C_4)$-alkyl is optionally substituted by radicals of the formula $-NH-CO-CH_3$ or $-NH-CO-CF_3$, or $R^4$ represents hydrogen, methyl, ethyl or acetyl, D represents an oxygen or sulphur atom, $R^5$ represents hydrogen, halogen or $(C_1-C_4)$-alkyl, and their salts.

Compounds of the general formulae (I) and (Ia) according to the invention are particularly preferred in which $R^1$ represents phenyl or thienyl, where the abovementioned ring systems are optionally substituted up to 2 times, in an identical or different manner, by substituents selected from the group consisting of fluorine, chlorine, methyl, trifluoromethyl or nitro, $R^2$ represents a radical of the formula $-OR^{12}$ or $-NR^{13}R^{14}$, in which $R^{12}$ represents hydrogen or $(C_1-C_4)$-alkyl, $R^{13}$ and $R^{14}$ are identical or different and denote hydrogen or methyl $R^3$ represents hydrogen or formyl, cyano, trifluoromethyl or cyclopropyl, or represents $(C_1-C_3)$-alkyl which is optionally substituted by fluorine, chlorine, hydroxyl, which for its part can be substituted up to 3 times by $C_1-C_3$-alkoxycarbonyl, $R^4$ represents hydrogen or methyl, D represents an oxygen or sulphur atom, $R^5$ represents hydrogen, fluorine, chlorine or $(C_1-C_3)$-alkyl, and their salts.

Compounds of the general formulae (I) and (Ia) according to the invention are very particularly preferred in which $R^1$ represents phenyl or thienyl, each of which is optionally substituted up to 2 times, in an identical or different manner, by fluorine or chlorine, $R^2$ represents methoxy, ethoxy or n-propoxy, $R^3$ represents hydrogen, methyl or cylcopropyl, $R^4$ represents hydrogen, D represents an oxygen or sulphur atom, $R^5$ represents hydrogen, fluorine or chlorine, and their salts.

In the context of the invention, cycloalkyl having 3 to 6 carbon atoms represents cyclopropyl, cyclopentyl, cyclobutyl, cyclohexyl. The following may be preferably mentioned: cyclopentyl or cyclohexyl.

Aryl in general represents an aromatic radical having 6 to 10 carbon atoms. Preferred aryl radicals are phenyl and naphthyl.

In the context of the invention, $(C_1-C_6)$-alkyl represents a straight-chain or branched acyl radical having 1 to 6 carbon atoms. A straight-chain or branched acyl radical having 1 to 4 carbon atoms is preferred. Preferred acyl radicals are acetyl and propionyl.

In the context of the invention, $(C_1-C_6)$-alkyl represents a straight-chain or branched alkyl radical having 1 to 6 carbon atoms. A straight-chain or branched alkyl radical having 1 to 4 carbon atoms is preferred.

The following may be mentioned as examples: methyl, ethyl, propyl, isopropyl, tert-butyl, n-pentyl and n-hexyl.

In the context of the invention, $(C_2-C_6)$-alkenyl represents a straight-chain or branched alkenyl radical having 2 to 6 carbon atoms. A straight-chain or branched alkenyl radical having 3 to 5 carbon atoms is preferred. Examples which may be mentioned are: ethenyl, propenyl, isopropenyl, tert-butenyl, n-pentenyl and n-hexenyl.

In the context of the invention, $(C_1-C_6)$-alkoxy represents a straight-chain or branched alkoxy radical having 1 to 6 carbon atoms. A straight-chain or branched alkoxy radical having 1 to 4 carbon atoms is preferred. Examples which may be mentioned are: methoxy, ethoxy, propoxy, isopropoxy, tert-butoxy, n-pentoxy and n-hexoxy.

In the context of the invention, $(C_1-C_6)$-alkoxycarbonyl represents a straight-chain or branched alkoxycarbonyl radical having 1 to 6 carbon atoms. A straight-chain or branched alkoxycarbonyl radical having 1 to 4 carbon atoms is preferred. Examples which may be mentioned are: methoxycarbonyl, ethoxycarbonyl, propoxycarbonyl, isopropoxycarbonyl, tert-butoxycarbonyl, n-pentoxycarbonyl and n-hexoxycarbonyl.

The compounds according to the invention can exist in stereoisomeric forms which either behave as image and mirror image (enantiomers), or which do not behave as image and mirror image (diastereomers). The invention relates both to the enantiomers or diastereomers and to their respective mixtures. Like the diastereomers, the racemic forms can also be separated into the stereoisomerically uniform constituents in a known manner.

The substances according to the invention can also be present as salts. In the context of the invention, physiologically acceptable salts are preferred.

Physiologically acceptable salts can be salts of the compounds according to the invention with inorganic or organic acids. Preferred salts are those with inorganic acids such as, for example, hydrochloric acid, hydrobromic acid, phosphoric acid or sulphuric acid, or salts with organic carboxylic or sulphonic acids such as, for example, acetic acid, maleic acid, fumaric acid, malic acid, citric acid, tartaric acid, lactic acid, benzoic acid, or methanesulphonic acid, ethanesulphonic acid, phenylsulphonic acid, toluenesulphonic acid or naphthalenedisulphonic acid.

Physiologically acceptable salts can also be metal or ammonium salts of the compounds according to the invention. Particularly preferred salts are, for example, sodium, potassium, magnesium or calcium salts, and also ammonium salts, which are derived from ammonia, or from organic amines, such as, for example, ethylamine, di- or triethylamine, di- or triethanolamine, dicyclohexylamine, dimethylaminoethanol, arginine, lysine, ethylenediamine or 2-phenylethylamine.

The compounds of the general formula (I) or (Ia) according to the invention can be prepared by a process
in which
[A] aldehydes of the general formula (II)

 $R^1$—CHO (II)

in which $R^1$ has the meaning indicated above,
are reacted with amidines or their hydrochlorides of the formula (III)

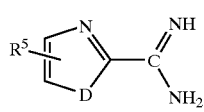 (III)

in which $R^5$ and D have the meaning indicated above,
and compounds of the general formula (IV)

 $R^3$—CO—CH$_2$—CO—R$^2$ (IV)

in which $R^2$ and $R^3$ have the meaning indicated above,
if appropriate in the presence of inert organic solvents with or without addition of base or acid, or

[B] compounds of the general formula (V)

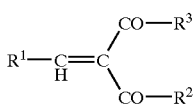 (V)

in which $R^1$, $R^2$ and $R^3$ have the meaning indicated above,
are reacted with amidines of the general formula (III)

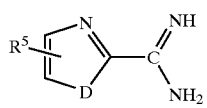 (III)

in which $R^5$ and D have the meaning indicated above,
if appropriate in the presence of inert organic solvents at temperatures between 20° C. and 150° C. with or without addition of base or acid, or

[C] aldehydes of the general formula (II)

 $R^1$—CHO (II)

in which $R^1$ has the meaning indicated above,
are reacted with compounds of the general formula (VI)

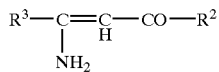 (VI)

in which $R^2$ and $R^3$ have the meaning indicated above,
and amidines of the general formula (III) as described above.

The processes according to the invention can be illustrated by way of example by the following reaction schemes:

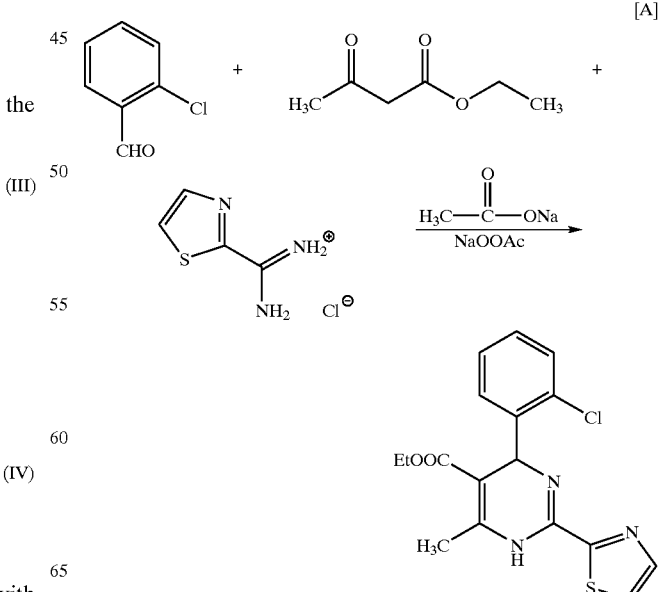

[A]

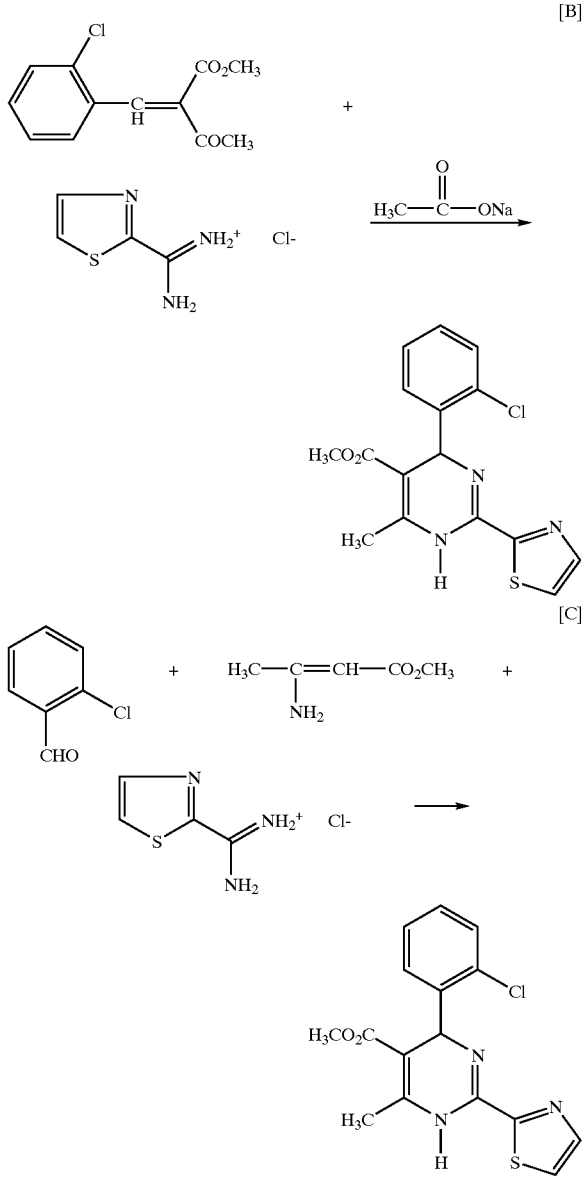

For all process variants A, B and C, suitable solvents are all inert organic solvents. These preferably include alcohols such as ethanol, methanol, isopropanol, ethers such as dioxane, diethyl ether, tetrahydrofuran, glycol monomethyl ether, glycol dimethyl ether or glacial acetic acid, dimethylformamide, dimethyl sulphoxide, acetonitrile, pyridine and hexamethylphosphoramide.

The reaction temperatures can be varied within a relatively wide range. In general, the reaction is carried out between 20 and 150° C., but preferably at the boiling temperature of the respective solvent.

The reaction can be carried out at normal pressure, but also at elevated pressure. In general, the reaction is carried out under normal pressure.

The reaction can be carried out with or without addition of base or acid, but it has been shown that a reaction within the meaning of the invention preferably takes place in the presence of relatively weak acids such as, for example, acetic acid or formic acid.

The aldehydes of the general formula (II) used as starting substances are known or can be prepared according to methods known from the literature [cf. T. D. Harris and G. P. Roth, J. Org. Chem. 44, 146 (1979), German Offenlegungsschrift 2 165 260, July 1972, German Offenlegungsschrift 2 401 665, July 1974, Mijano et al., Chem. Abstr. 59, (1963), 13 929 c, E. Adler and H.-D. Becker, Chem. Scand. 15, 849 (1961), E. P. Papadopoulos, M. Mardin and Ch. Issidoridis, J. Org. Chem. Soc. 78, 2543 (1956)].

The amidines of the general formula (III) used as starting substances are known in some cases or can be prepared according to methods known from the literature [cf. Houben-Weyl, Methoden der organischen Chemie [Methods of organic chemistry], Vol. 11/2, page 38 ff (1958); R. L. Shoiner and F. W. Neumann, Chem. Review 35, 351 (1944)].

The β-ketocarboxylic acid esters of the general formula (IV) used as starting substances are known or can be prepared according to methods known from the literature [e.g. D Borrmann, "Umsetzung von Diketen mit Alkoholen, Phenolen and Mercaptanen" [Reaction of diketene with alcohols, phenols and mercaptans], in Houben-Weyl, Methoden der organischen Chemie [Methods of organic chemistry], Vol. VII/4, 230 ff (1968); Y. Oikawa, K. Sugano and O. Yonemitsu, J. Org. Chem. 43, 2087 (1978)].

The ylidene-β-ketoesters of the formula (V) used as starting substances can be prepared by methods known from the literature [cf. G. Jones, "The Knoevenagel Condensation", in Organic Reactions, Vol. XV, 204 ff. (1967)].

The enaminocarboxylic acid esters of the formula (VI) used as starting substances are known or can be prepared by methods known from the literature [cf. A. C. Cope, J. Am. Chem. Soc. 67, 1017 (1945)].

The antiviral action of the compounds according to the invention was determined following the methods described by Sells et al. (M. A. Sells, M.-L. Chen, and G. Acs (1987) Proc. Natl. Acad. Sci. 84, 1005–1009) and Korba et al. (B. E. Korba and J. L. Gerin (1992) Antiviral Research 19, 55–70).

The antiviral tests were carried out in 96-well microtitre plates. The first vertical row of the plate contained only growth medium and HepG2.2.15 cells. It was used as a virus control.

Stock solutions of the test compounds (50 mM) were first dissolved in DMSO, further dilutions of the hepatitis B virus-producing HepG2.2.15 cells were prepared in growth medium. As a rule, the compounds according to the invention were each pipetted into the second vertical test row of the microtitre plate in a test concentration of 100 $\mu$M (1st test concentration) and then diluted $2^{10}$ times in steps of 2 in growth medium plus 2% foetal calf serum (volume 25 $\mu$l).

Each well of the microtitre plate then contained 225 $\mu$l of a HepG2.2.15 cell suspension (5×10 cells/ml) in growth medium plus 2% foetal calf serum.

The test mixture was incubated for 4 days, 37° Celsius, 5% $CO_2$.

The supernatant was then aspirated and discarded, and the wells received 225 $\mu$l of freshly prepared growth medium. The compounds according to the invention were each added again as a 10-fold concentrated solution in a volume of 25 $\mu$l. The mixtures were incubated for a further 4 days.

Before the harvesting of the supernatants to determine the antiviral effect, the HepG2.2.15 cells were investigated for cytotoxic changes by light microscopy or by means of biochemical detection procedures (e.g. Alamar Blue staining or Trypan Blue staining).

The supernatants were then harvested and absorbed by means of vacuum on 96-well dot blot chambers covered with nylon membrane (according to the manufacturer's instructions).

Cytotoxicity Determination

Substance-induced cytotoxic or cytostatic changes in the HepG2.2.15 cells were determined, for example, by light microscopy as changes in the cell morphology. Substance-induced changes of this type in the HHepG2.2.15 cells in comparison with untreated cells were visible, for example, as cell lysis, vacuolization or modified cell morphology. 50% toxicity (tox. 50) means that 50% of the cells have a morphology comparable to the corresponding cell control.

The tolerability of some of the compounds according to the invention was additionally tested on other host cells such as, for example, HeLa cells, primary peripheral human blood cells or transformed cell lines such as H-9 cells. It was not possible to determine any cytotoxic changes at concentrations of >10 μM of the compounds according to the invention.

Determination of the Antiviral Action

In brief; after transfer of the supernatants to the nylon membrane of the dot blot apparatus (see above), the supernatants of the HepG2.2.15 cells were denatured (1.5M NaCl/0.5N NaOH), neutralized (3M NaCl/0.5M tris HCl, pH 7.5) and washed (2×SSC). The DNA was then baked onto the membrane by incubation of the filters at 120° C., 2–4 hours.

Hybridization of the DNA

As a rule, the detection of the viral DNA of the treated HepG2.2.15 cells on the nylon filters was carried out using non-radioactive, digoxigenin-labelled hepatitis B-specific DNA probes, which in each case were labelled according to the manufacturer's instructions, purified and employed for hybridization.

Briefly: the prehybridization and hybridization was carried out in 5×SSC, 1×blocking reagent, 0.1% N-lauroylsarcosine, 0.02% SDS and 100 μg of herring sperm DNA. Prehybridization was carried out for 30 minutes at 60° C., specific hybridization using 20–40 ng/ml of the digoxigeninated, denatured HBV-specific DNA (14 hours. 60° C.). The filters were then washed.

Detection of the HBV DNA by Digoxigenin Antibodies

The immunological detection of the digoxigenin-labelled DNA was carried out according to the manufacturer's instructions. Briefly: the filters were washed and prehybridized in a blocking reagent (according to the manufacturer's instructions). Hybridization was then carried out with an anti-DIG antibody, which had been coupled to alkaline phosphatase. After a washing step, the substrate of the alkaline phosphatase, CSPD, was added and incubated with the filters for 5 minutes, which were then wrapped in plastic film and incubated at 37° C. for a further 15 minutes. The chemiluminescence of the hepatitis B-specific DNA signals was visualized by means of exposure of the filters to an X-ray film (incubation depending on signal strength: 10 minutes to 2 hours). The half-maximal inhibitory concentration (IC-50, inhibitory concentration 50%) was determined as the concentration at which, compared with an untreated sample, the hepatitis B-specific band was reduced by 50% by the compound according to the invention.

The treatment of the hepatitis B virus-producing HepG2.2. 15 cells with the compounds according to the invention surprisingly led to a reduction of viral DNA in the cell culture supernatant, which is expelled from the cells into the cell culture supernatant in the form of virions.

The compounds according to the invention exhibit a new, unforeseeable and valuable action against viruses. They are surprisingly antivirally active against hepatitis B (HBV) and are thus suitable for the treatment of virus-induced diseases, in particular of acute and chronic persistent HBV virus infections. A chronic viral disease produced by HBV can lead to syndromes of differing severity; as is known, chronic hepatitis B virus infection in many cases leads to liver cirrhosis and/or to hepatocellular carcinoma.

Examples which may be mentioned of indication areas for the compounds utilizable according to the invention are:

The treatment of acute and chronic viral infections which can lead to infectious Hepatitis, for example infections with hepatitis B viruses. The treatment of chronic hepatitis B infections and the treatment of acute hepatitis B viral infections are particularly preferred.

The present invention includes pharmaceutical preparations which, in addition to non-toxic, inert pharmaceutically suitable excipients, comprise one or more compounds of the formulae (I) and (Ia) or which consist of one or more active compounds of the formula (I), and processes for the production of these preparations.

The active compounds of the formulae (I) and (Ia) should be present in the abovementioned pharmaceutical preparations in a concentration of approximately 0.1 to 99.5% by weight, preferably of approximately 0.5 to 95% by weight, of the total mixture.

Apart from the compounds of the formulae (I) and (Ia), the abovementioned pharmaceutical preparations can also comprise further pharmaceutical active compounds.

The abovementioned pharmaceutical preparations are prepared in a customary manner by known methods, e.g. by mixing the active compound(s) with the excipient(s).

In general, it has proved advantageous both in human and in veterinary medicine to administer the active compounds according to the invention in total amounts of approximately 0.5 to approximately 500, preferably 1 to 100, mg/kg of body weight every 24 hours, if appropriate in the form of a number of individual doses, to achieve the desired results. An individual dose contains the active compound(s) preferably in amounts from approximately 1 to 80, in particular 1 to 30, mg/kg of body weight. However, it may be necessary to depart from the doses mentioned, namely depending on the species and the body weight of the subject to be treated, the nature and the severity of the disease, the type of preparation and the administration of the medicament, and the period or interval within which administration takes place.

Starting Compounds

EXAMPLE I

2-Amidino-thiazole hydrochloride

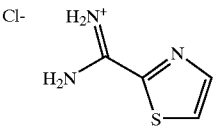

4.5 g of sodium (0.2 mol) are added in portions to 220 ml of MeOH. After formation of the methoxide, 22.9 g (0.21 mol) of 2-cyano-thiazole (J. Chem. Soc. C, 1967, p. 517) are added and the mixture is stirred at RT for two days. Inorganic salts are filtered off with suction, the mixture is concentrated, the residue is crystallized using a little acetone and the product is filtered off with suction. 17.4 g (51%) 2-amidino-thiazole hydrochloride.

M.p.: 188° C., dec.

$R_f$: 0.26 (EA/MeOH/$H_2O$/conc. $NH_3$=6:3:0.5:0.05)

PREPARATION EXAMPLES

Example 1

Methyl 4-(2-chlorophenyl)-6-methyl-2-(thiazol-2-yl)-1,4-dihydropyrimidine-5-carboxylate

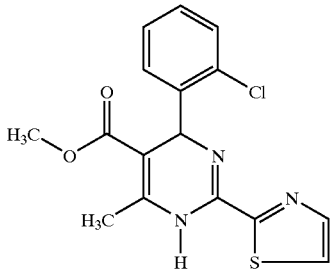

320 mg (2 mmol) of 2-amidino-thiazole hydrochloride, 470 mg (2 mmol) of methyl 2-chlorobenzylidene-acetoacetate and 100 mg (2.4 mmol) of sodium acetate are refluxed for 16 h in 10 ml of ethanol. The mixture is concentrated, rendered alkaline with dil. NaOH and extracted by shaking with EA. After purification on silica gel (cyclohexane: EA=7:3), 350 mg (32%) of substance are obtained.

$R_f$=0.23 (cyclohexane/EA=7:3)

Example 2

Methyl 4-(4-chlorophenyl)-6-methyl-2-(thiazol-2-yl)-1,4-dihydropyrimidine-5-carboxylate

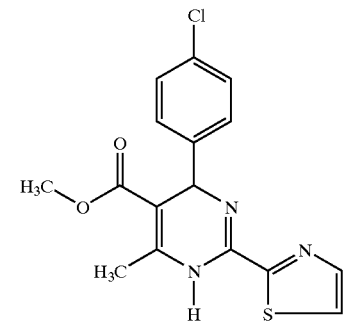

270 mg (1.7 mmol) of 2-amidino-thiazole, 200 mg (1.7 mmol) of methyl acetoacetate, 230 mg (1.7 mmol) of 4-chlorobenzaldehyde and 165 mg (2 mmol) of sodium acetate are refluxed for 16 h in 11 ml of ethanol. Work-up as in Example 1 affords 350 mg (31%) of amorphous substance.

$R_f$=0.20 (cyclohexane/EA=7:3)

The compounds shown in Table 1 are prepared analogously to the procedure of Example 2:

TABLE 1

| Example No. | Structure | Yield | $R_f$/m.p./$[\alpha]_D$ |
|---|---|---|---|
| 3 | 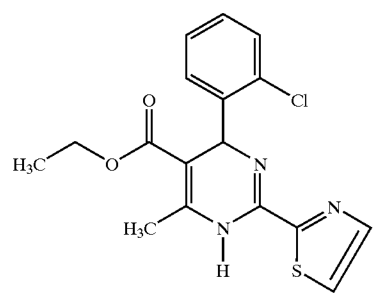 | 34% | 0.31 |
| 4 | 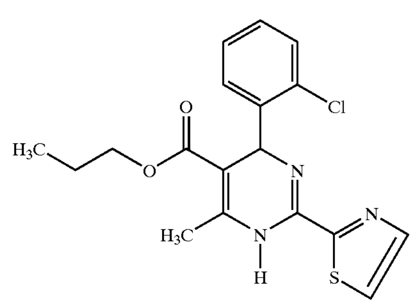 | 33% | 0.33 |

TABLE 1-continued

| Example No. | Structure | Yield | $R_f$/m.p./$[\alpha]_D$ |
|---|---|---|---|
| 5 | 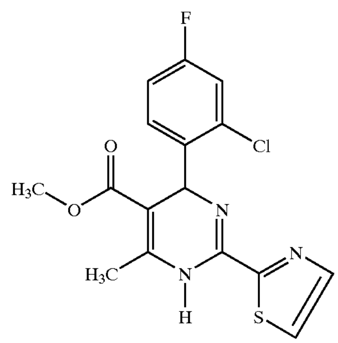 | 23% | 0.28 |
| 6 Preparation was carried out in 2-propanol. | | 36% | 0.30/154° C. |
| 7 | 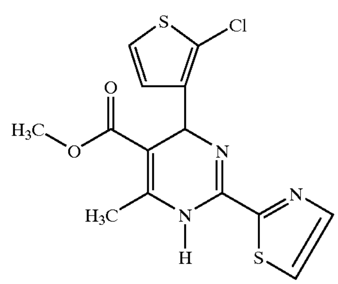 | 27% | 0.22 |
| 8 | 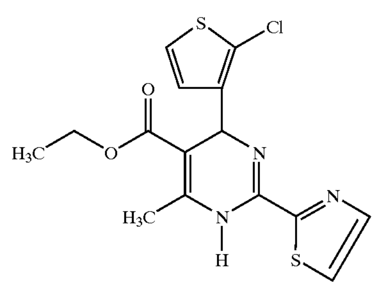 | 15% | 0.28 |

TABLE 1-continued

| Example No. | Structure | Yield | $R_f$/m.p./$[\alpha]_D$ |
|---|---|---|---|
| 9 (−)-Enantiomer of Example 6 | 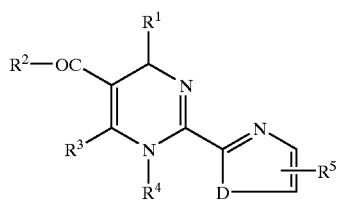 | Separation of 6 on chiral columns | $[\alpha]_D = -52.0°$ (CH$_3$OH) |
| 10 | 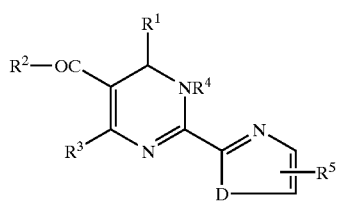 | | 0.33 (cyclohexane/ EA = 7:3) |

$R_f$ = the distance of a substance from the starting point divided by the distance of the solvent front, likewise from the starting point
M.p. = Melting point
$[\alpha]_D^0$ = Specific rotation
EA = Ethyl acetate

What is claimed is:
1. A dihydroxypyrimidine of the general formula (I)

(I)

or its isomeric form (Ia)

(Ia)

in which

R$^1$ represents phenyl, furyl, thienyl, pyridyl, cycloalkyl having 3 to 6 carbon atoms or a radical of the formula

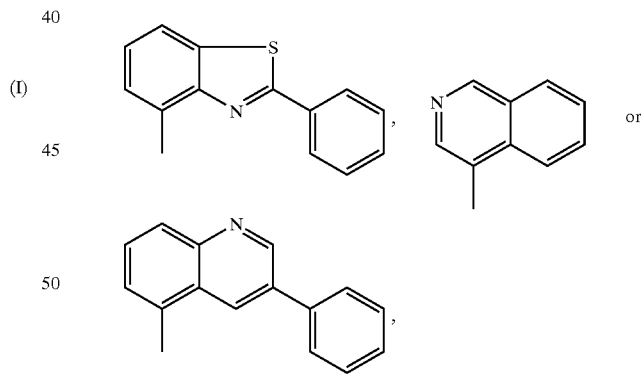

where the abovementioned ring systems are optionally monosubstituted or polysubstituted in an identical or different manner, by substituents selected from the group consisting of halogen, trifluoromethyl, nitro, cyano, trifluoromethoxy, carboxyl, hydroxyl, (C$_1$–C$_6$)-alkoxy, (C$_1$–C$_6$)-alkoxycarbonyl and (C$_1$–C$_6$)-alkyl, which for its part can be substituted by aryl having 6 to 10 carbon atoms or halogen, and/or the ring systems mentioned are optionally substituted by groups of the formula —S—R$^6$, NR$^7$R$^8$, CO—NR$^9$R$^{10}$, SO$_2$—CF$_3$ and —A—CH$_2$—R$^{11}$, in which R$^6$ is phenyl which is optionally substituted by halogen, R$^7$, R$^8$, R$^9$ and R$^{10}$ are identical or different and are hydrogen, phenyl, hydroxy-substituted phenyl, hydroxyl, (C$_1$–C$_6$)-acyl or (C$_1$–C$_6$)-alkyl, which for its part can be substituted by hydroxyl, (C$_1$–C$_6$)-alkoxycarbonyl, phenyl or hydroxy-substituted phenyl, A is a radical O, S, SO or SO$_2$, R$^{11}$ is phenyl which is optionally mono- to polysubstituted, in an identical or different manner, by substituents selected from the group consisting of halogen, nitro, trifluoromethyl, (C$_1$–C$_6$)-alkyl and (C$_1$–C$_6$)-alkoxy, R$^2$ represents a radical of the formula —OR$^{12}$ or —NR$^{13}$R$^{14}$, in which R$^{12}$ is hydrogen, (C$_1$–C$_6$)-alkoxycarbonyl or a straight-chain, branched or cyclic, saturated or unsaturated (C$_1$–C$_8$)-hydrocarbon radical which optionally contains one or two identical or different hetero chain members from the group consisting of O, CO, NH, —N—(C$_1$–C$_4$)-alkyl, —N—((C$_1$–C$_4$)-alkyl)$_2$, S and SO$_2$ and which is optionally substituted by halogen, nitro, cyano, hydroxyl, aryl having 6 to 10 carbon atoms or aralkyl having 6 to 10 carbon atoms, or a group of the formula —NR$^{15}$R$^{16}$, in which R$^{15}$ and R$^{16}$ are identical or different and are hydrogen, benzyl or (C$_1$–C$_6$)-alkyl, R$^{13}$ and R$^{14}$ are identical or different and are hydrogen, (C$_1$–C$_6$)-alkyl or cycloalkyl having 3 to 6 carbon atoms, R$^3$ represents hydrogen, amino or a radical of the formula

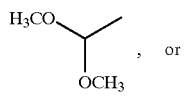
, or formyl, cyano or trifluoromethyl, or a straight-chain, branched or cyclic, saturated or unsaturated hydrocarbon radical having up to 8 carbon atoms, which is optionally mono- or polysubstituted, in an identical or different manner, by aryloxy having 6 to 10 carbon atoms, azido, cyano, hydroxyl, carboxyl, (C$_1$–C$_6$)-alkoxycarbonyl, (C$_1$–C$_6$)-alkylthio, (C$_1$–C$_6$)-alkoxy, which for its part can be substituted by azido or amino, and/or is substituted by triazolyl which for its part can be substituted up to 3 times by (C$_1$–C$_6$)-alkoxycarbonyl, and/or can be substituted by groups of the formula —OSO$_2$—CH$_3$ or (CO)$_a$—NR$^{17}$R$^{18}$, in which a is a number 0 or 1, R$^{17}$ and R$^{18}$ are identical or different and are hydrogen or aryl, aralkyl having 6 to 10 carbon atoms, or are (C$_1$–C$_6$)-alkyl which is optionally substituted by (C$_1$–C$_6$)-alkoxycarbonyl, hydroxyl, phenyl or benzyl, where phenyl or benzyl are optionally mono- or polysubstituted, in an identical or different manner, by hydroxyl, carboxyl (C$_1$–C$_6$)-alkyl or (C$_1$–C$_6$)-alkoxy, NH—CO—CH$_3$ or NH—CO—CF$_3$, R$^4$ represents hydrogen, (C$_1$–C$_4$)-alkyl, acetyl or benzoyl, D represents an oxygen or sulphur atom, R$^5$ represents hydrogen, halogen or straight-chain or branched alkyl having up to 6 carbon atoms, or a salt thereof.

2. A dihydropyrimidine according to claim 1, in which

R$^1$ represents phenyl, furyl, thienyl, pyridyl, cyclopentyl or cyclohexyl, where the abovementioned ring systems are optionally substituted one or 2 times, in an identical or different manner, by substituents selected from the group consisting of halogen, trifluoromethyl, nitro, SO$_2$—CF$_3$, methyl, cyano, trifluoromethoxy, carboxyl, methoxycarbonyl or radicals of the formulae —CO—NH—CH$_2$—C(CH$_3$)$_3$, —CO—NH(CH$_2$)$_2$OH, —CO—NH—CH$_2$—C$_6$H$_5$, —CO—NH—C$_6$H$_5$, —O—CH$_2$—C$_6$H$_5$, —CO—NH—C$_6$H$_4$-pOH, or —S—C$_6$H$_4$-pCl;

R$^2$ represents a radical of the formula —OR$^{12}$ or —NR$^{13}$R$^{14}$, in which R$^{12}$ is hydrogen, (C$_1$–C$_4$)-alkenyl or (C$_1$–C$_4$)-alkyl, which is optionally substituted by cyano, benzyl or by a radical of the formula —NR$^{15}$R$^{16}$, in which R$^{15}$ and R$^{16}$ are identical or different and are hydrogen, methyl or ethyl, R$^{13}$ and R$^{14}$ are identical or different and are hydrogen, methyl, ethyl or cyclopropyl, R$^3$ represents hydrogen or a radical of the formula

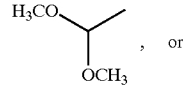
, or represents formyl, cyano, trifluoromethyl or cyclopropyl, or represents (C$_1$–C$_4$)-alkyl which is optionally substituted by radicals of the formula —SO$_2$CH$_3$, —NH—CO—CH$_3$, —NH—CO—CF$_3$, (C$_1$-C$_3$)-alkoxycarbonyl or hydroxyl, and/or alkyl is optionally substituted by groups of the formula —OSO$_2$—CH$_3$ or (CO)$_a$—NR$^{17}$R$^{18}$, in which a is a number 0 or 1, R$^{17}$ and R$^{18}$ are identical or different and are hydrogen, phenyl or benzyl, or are C$_1$–C$_4$-alkyl which is optionally substituted by (C$_1$–C$_4$)-alkoxycarbonyl, hydroxyl, phenyl or benzyl, where phenyl or benzyl are optionally mono- or polysubstituted, in an identical or different manner, by hydroxyl, carboxyl, (C$_1$–C$_4$)-alkyl or (C$_1$–C$_4$)-alkoxy, —NH—CO—CH$_3$ or —NH—CO—CF$_3$, or R$^4$ represents hydrogen, methyl, ethyl or acetyl, D represents an oxygen or sulphur atom, R$^5$ represents hydrogen, halogen or (C$_1$–C$_4$)-alkyl, or a salt thereof.

3. A dihydropyrimidine according to claim 1 or 2, in which

R$^1$ represents phenyl or thienyl, where the abovementioned ring systems are optionally substituted up to 2 times, in an identical or different manner, by substituents selected from the group consisting of fluorine, chlorine, methyl, trifluoromethyl or nitro, R$^2$ represents a radical of the formula —OR$^{12}$ or —NR$^{13}$R$^{14}$, in which $R^{12}$ represents hydrogen or $(C_1-C_4)$-alkyl, $R^{13}$ and $R^{14}$ are identical or different and are hydrogen or methyl, $R^3$ represents hydrogen or formyl, cyano, trifluoromethyl or cyclopropyl, or represents $(C_1-C_3)$-alkyl which is optionally substituted by hydroxyl, $R^4$ represents hydrogen or methyl, D represents an oxygen or sulphur atom, $R^5$ represents hydrogen, fluorine, chlorine or $(C_1-C_3)$-alkyl, or a salt thereof.

4. A dihydropyrimidine according to claim 1, in which $R^1$ represents phenyl or thienyl, each of which is optionally substituted up to 2 times, in an identical or different manner, by fluorine or chlorine, $R^2$ represents methoxy, ethoxy or n-propoxy, $R^3$ represents hydrogen, methyl or cylcopropyl, $R^4$ represents hydrogen, D represents an oxygen or sulphur atom, $R^5$ represents hydrogen, fluorine or chlorine or a salt thereof.

5. A pharmaceutical composition, comprising at least one compound of the general formula (I) or (Ia) according to claim 1 and a pharmaceutically acceptable auxiliary or excipient.

\* \* \* \* \*